US00PP24794P3

(12) United States Plant Patent
van der Velden

(10) Patent No.: US PP24,794 P3
(45) Date of Patent: Aug. 19, 2014

(54) *PEPEROMIA* PLANT NAMED 'HOPE'

(50) Latin Name: *Peperomia deppeana×quadrifolia*
Varietal Denomination: HOPE

(76) Inventor: Josephus M. van der Velden, Sint-Oedenrode (NL)

( * ) Notice: Subject to any disclaimer, the term of this patent is extended or adjusted under 35 U.S.C. 154(b) by 203 days.

(21) Appl. No.: 13/507,153

(22) Filed: Jun. 7, 2012

(65) Prior Publication Data

US 2013/0333085 P1 Dec. 12, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Wendy C Haas
(74) *Attorney, Agent, or Firm* — Cassandra Bright

(57) ABSTRACT

A new and distinct *Peperomia* cultivar named 'HOPE' is disclosed, characterized by unique leaf shape, vigorous growth and good shelf life. The new variety is a *Peperomia,* normally produced as an indoor ornamental plant.

1 Drawing Sheet

Latin name of the genus and species: *Peperomia deppeana×quadrifolia.*
Variety denomination: 'HOPE'.

BACKGROUND OF THE INVENTION

The new *Peperomia* cultivar is a product of a planned breeding program conducted by the inventor, Josephus van der Velden, in Sint-Oedenrode, The Netherlands. The objective of the breeding program was to produce new *Peperomia* varieties for ornamental commercial applications. The cross resulting in this new variety was made during February 2007

The seed parent is the unpatented variety referred to as *Peperomia deppeana.* The pollen parent is an unnamed variety of *Peperomia quadrifolia,* The new variety was discovered in July 2007 by the inventor in a group of seedlings resulting from the February crossing, in a commercial nursery at Sint-Oedenrode, The Netherlands.

Asexual reproduction of the new cultivar 'HOPE' by vegetative cuttings was first performed at a commercial nursery Sint-Oedenrode, The Netherlands in the Summer of 2008 and has shown that the unique features of this cultivar are stable and reproduced true to type in successive generations.

SUMMARY OF THE INVENTION

The cultivar 'HOPE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOPE' These characteristics in combination distinguish 'HOPE' as a new and distinct *Peperomia* cultivar:

1. Unique leaf shape
2. Vigorous growth
3. Good shelf life

PARENTAL COMPARISON

Plants of the new cultivar 'HOPE' are similar to plants of the seed parent, *Peperomia deppeana* in most horticultural characteristics, however, plants of the new cultivar 'HOPE' produce bigger and thicker leaves that are more resistant to physical stress.

Plants of the new cultivar 'HOPE' are similar to plants of the pollen parent, *Peperomia quadrifolia* in most horticultural characteristics, however, plants of the new cultivar 'HOPE' produce thicker leaves of brighter green color, as well shorter internodes.

COMMERCIAL COMPARISON

Plants of the new cultivar 'HOPE' are best compared to the parent varieties.

BRIEF DESCRIPTION OF THE PHOTOGRAPH

The accompanying photograph in FIG. 1 illustrates in full color a typical plant of 'HOPE' grown in a greenhouse, in a 12 cm pot. Age of the plant photographed is approximately 5 months old from a rooted cutting. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'HOPE' plants grown in a greenhouse during spring in Sint-Oedenrode, The Netherlands. The growing temperature was approximately 75° F. during the day and 68° F. during the night. General light conditions are bright, normal sunlight. Measurements and numerical values represent averages of typical plant types. Plants are approximately 5 months old from a rooted cutting.

Botanical classification: *Peperomia deppeana×quadrifolia* 'HOPE'.

PROPAGATION

Time to produce a rooted cutting: About 25 days at approximately 20° C.

Description of roots: Thin, densely branched, moderately fibrous, non-fleshy, coloured near RHS 199D to 156D.

PLANT

Plant spread: Approximately 19.6 cm.
Growth rate: Moderate.
Length of primary stems: Approximately 14.2 cm.
Quantity of primary stems: About 5.
Stem:
*Color.*—Near RHS 152C, densely dotted and marbled 178B.
*Texture/pubescence.*—Smooth, moderately glossy.
*Diameter.*—Average: 4 mm.
*Length.*—Approximately 14.2 cm (no secondary stems present, only primary stems).
*Strength.*—Moderately strong.
Age of plant described: Approximately 5 months from a rooted cutting.

FOLIAGE

Leaf:
*Arrangement.*—Opposite to whorls of four.
*Quantity.*—Approximately 15 per stem.
*Average length.*—Approximately 3.0 cm.
*Average width.*—Approximately 2.8 cm.
*Shape of blade.*—Broad obovate to near orbicular.
*Apex.*—Rounded to bluntly short acute.
*Base.*—Obtuse to truncate.
*Margin.*—Entire.
*Texture of top surface.*—Smooth, slightly glossy.
*Texture of bottom surface.*—Smooth, dull.
*Color.*—Young foliage upper side: Near RHS 145B. Young foliage under side: Near RHS 154C to 154D, tinged 186D. Mature foliage upper side: Near RHS 137B to N137B. Mature foliage under side: Near RHS 146C.
*Venation.*—Type: Laciniate. Venation color upper side: Near RHS 143A. Venation color under side: Near RHS 146D.
*Petiole.*—Average Length: Approximately 0.4 cm. Diameter: Approximately 0.2 cm. Texture: Smooth, dull. Strength: Moderate. Color: Near RHS 199A to 199B.

FLOWER

No flowering observed to date.

OTHER CHARACTERISTICS

Disease/pest resistance: Neither resistance nor susceptibility to pathogens and pests common to *Peperomia* have been observed.
Temperature tolerance: The new variety exhibits standard temperature tolerance range for *Peperomia*.

What is claimed is:

1. A new and distinct cultivar of *Peperomia* plant named 'HOPE' as herein illustrated and described.

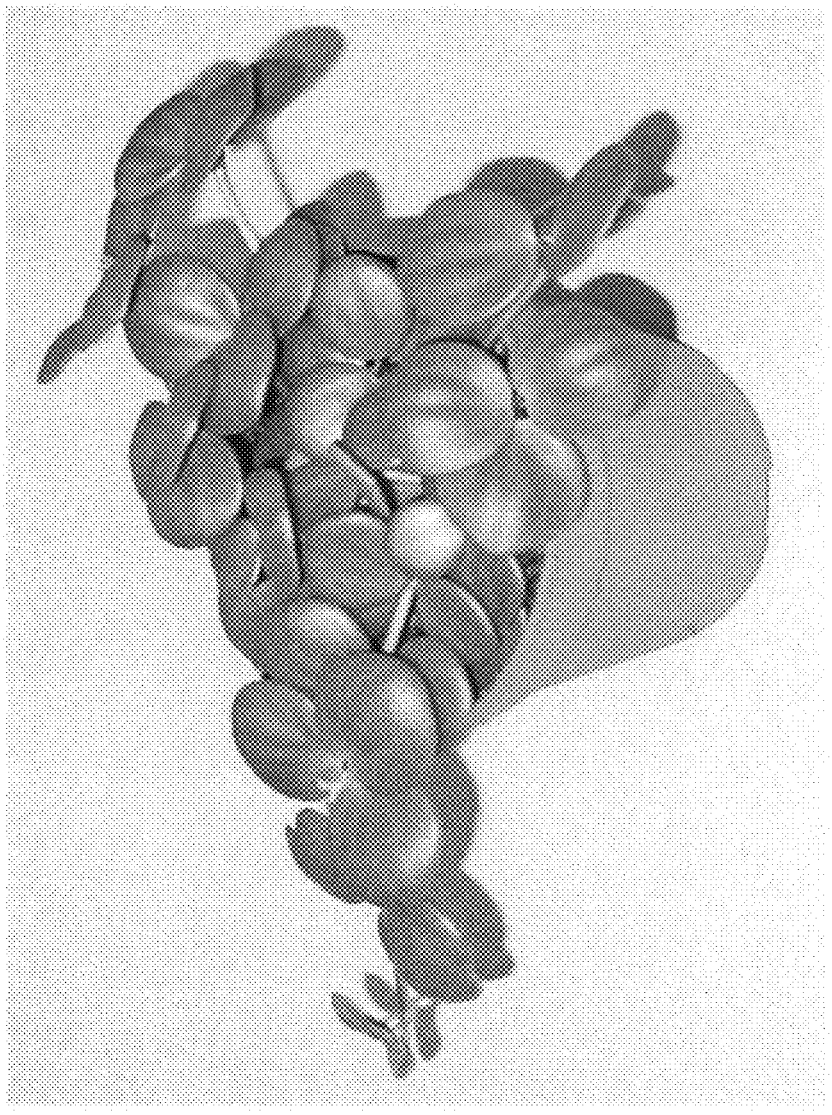

* * * * *